(12) United States Patent
Bruggraber et al.

(10) Patent No.: US 7,811,609 B2
(45) Date of Patent: *Oct. 12, 2010

(54) USE OF METAL COMPOUNDS TO TREAT GASTROINTESTINAL INFECTIONS

(75) Inventors: Sylvaine Franciose Aline Bruggraber, Channel Islands (GB); Jonathan Joseph Powell, London (GB)

(73) Assignee: Pfylori Limited, London (GB)

( * ) Notice: Subject to any disclaimer, the term of this patent is extended or adjusted under 35 U.S.C. 154(b) by 474 days.

This patent is subject to a terminal disclaimer.

(21) Appl. No.: 10/296,486

(22) PCT Filed: May 24, 2001

(86) PCT No.: PCT/GB01/02277

§ 371 (c)(1),
(2), (4) Date: Feb. 10, 2003

(87) PCT Pub. No.: WO01/89534

PCT Pub. Date: Nov. 29, 2001

(65) Prior Publication Data

US 2003/0180381 A1 Sep. 25, 2003

(30) Foreign Application Priority Data

May 24, 2000 (GB) .................................. 0012487.5

(51) Int. Cl.
*A01N 59/16* (2006.01)
*A61K 33/26* (2006.01)

(52) U.S. Cl. ....................................... 424/646; 514/184

(58) Field of Classification Search .................. 424/646; 514/501, 184

See application file for complete search history.

(56) References Cited

U.S. PATENT DOCUMENTS

| 4,326,523 A | * | 4/1982 | Wolfrom et al. | ............ 424/426 |
| 5,304,540 A | * | 4/1994 | Blackburn et al. | ............. 514/2 |
| 6,197,763 B1 | | 3/2001 | Thompson et al. | |

FOREIGN PATENT DOCUMENTS

| EP | 0770391 | | 5/1997 |
| EP | 0770391 | A | 5/1997 |
| EP | 1 170 013 | A1 | 1/2002 |
| GB | 756825 | | 9/1956 |
| WO | WO 97/36599 | | 10/1997 |
| WO | WO 97/36599 | A | 10/1997 |
| WO | WO 98/10773 | | 3/1998 |
| WO | WO 98/10773 | A | 3/1998 |
| WO | WO 98/16218 | | 4/1998 |

OTHER PUBLICATIONS

Hermann et al.,"Helicobacter pylori cadA encodes an essential Cd(II)-Zn(II)-Co(II) resistance factor influencing urease activity", Molecular Microbiology (1999), vol. 33, No. 3, pp. 524-536.*
Chohan, Z., Biological Role of Cobalt (II), Department of Chemistry, Pakistan, 1996, p. 69-74.*
Chohan, Zahid Hussain, et al., "Pharmacological Role of Anions (Sulphate, Nitrate, Oxalate and Acetate) on the Antibacterial Activity of Cobalt(II), Copper(II) and Nickel(II) Complexes with Nicotinoylhydrazine—Derived ONO, NNO and SNO Ligands", Metal-based drugs, 3, 1996, pp. 211-217.
Gerard, Christian, "Etudes des Complexes Neutres de l'acide Kojique et du Mallot Avec les Cations Divalents: Mn, Co, Ni, Cu et Zn", Bulletine Society Chim. Fr., 1979, pp. 451-456.
Mobley, Harry L.T. et al., "Role of Hpn and NixA of *Helicobacter pylori* in Susceptibility and Resistance to Bismuth and Other Metal Ions", Helicobacter, vol. 4, No. 3, 1999, pp. 162-169.
Morita, Hideyoshi et al., "The Syntheses and Properties of Bis(3-hydroxy-2-methyl-4-pyronato) Complexes of Bivalent Metal Ions", Bulletin of the Chemical Society of Japan, vol. 49(9), 1976, pp. 2461-2464.
Morita, Hideyoshi, et al., "Mixed Ligand Complexes Derived from the Reactions of Diaquabis-(3-hydroxy-2-methyl-4-pyronato)-cobalt(II),-nickel(II), and -zinc(II) with Pyridine and 4-Substituted Pyridines", Bulletin of the Chemical Society of Japan, vol. 51(11), 1978, pp. 3213-3217.
Perez-Perez, Guillermo J., et al., "Effects of Cations on *Helicobacter pylori* Urease Activity, Release, and Stability," Infect. and Immun., 62(1), 1994, pp. 299-302.
Thompson, G.A., et al., "Comparative Study of the Toxicity of Metal Compounds to Heterotrophic Bacteria", bull. Environ. Contam. Toxicol., 33, 1984, pp. 114-120.
Perez-Perez, Guillermo I., et al., "Effects of cations on *Helicobacter pylori* urease activity, release, and stability", *Infect. Immun.* (1994), 62(1), 299-302, XP001021659, abstract, p. 301.
Robinson, J.C. et al., "The Effect of Oral Therapy with Cobaltous Chloride on the Blood of Patients Suffering with Chronic Suppurative Infection," The New England Journal of Medicine, vol. 240, No. 19, 749-753, 1949.

* cited by examiner

*Primary Examiner*—Johann R Richter
*Assistant Examiner*—Danielle Sullivan
(74) *Attorney, Agent, or Firm*—Kilpatrick Stockton LLP

(57) ABSTRACT

Cobalt salts have been found to be particularly effective against *H. pylori* and may therefore be used to treat gastrointenstinal infection with this bacteria. The cobalt salts have the advantage of showing a good degree of selectivity for *H. pylori* over other Gram positive and Gram negative bacteria. Treatment with the cobalt salts may be carried out at the same time as conventional treatment with an antibiotic and/or a proton pump inhibitor.

26 Claims, 1 Drawing Sheet

USE OF METAL COMPOUNDS TO TREAT GASTROINTESTINAL INFECTIONS

Figure 1:
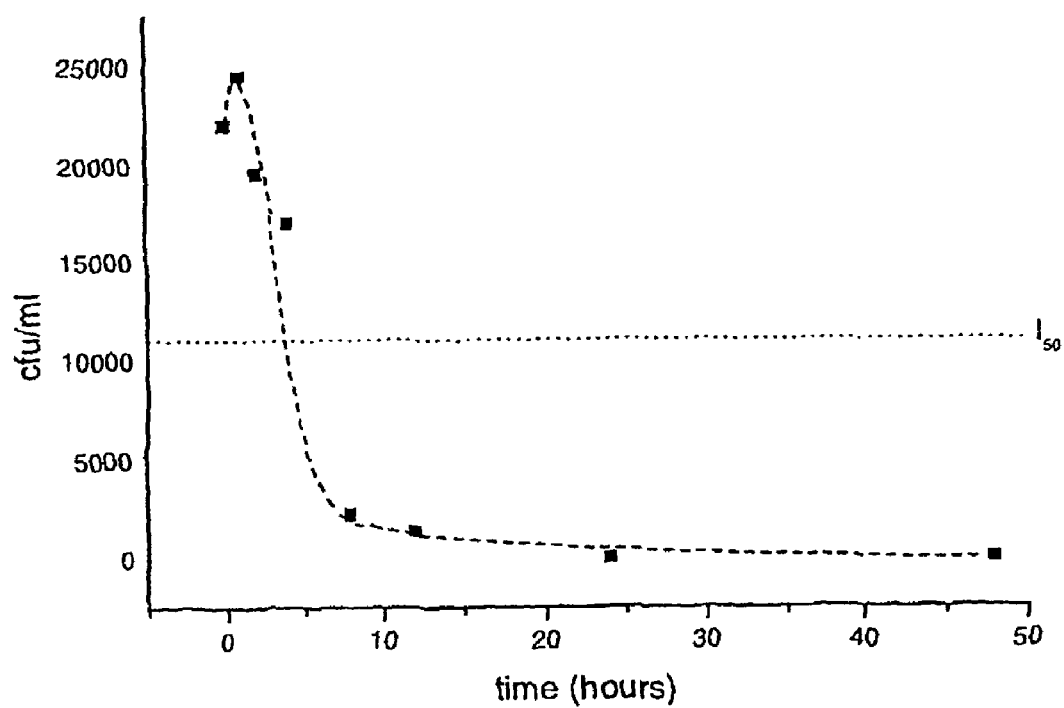

This invention relates to the use of cobalt salts to treat or prevent gastrointestinal infections. The invention also relates to pharmaceutical compositions comprising a cobalt salt and which are adapted for controlled release of cobalt ions or which comprise an antibiotic and/or a proton pump inhibitor and to methods of treating or preventing gastrointestinal infections using cobalt salts.

Gastrointestinal infections cause widespread diarrhoea and debility and account for a large proportion of antibiotic use worldwide. The non-specificity of antibiotics has meant that resistant pathogens are an increasing problem leading to more complex treatments. Furthermore, many antibiotics have side effects that reduce compliance, while cost may preclude their use in developing countries where infections are more common. Even in the western world, complex treatment is often required, for example, *H. pylori* infection of the gastric mucosa requires "triple therapy" for successful eradication. There are however few gut-specific antimicrobials so antibiotics designed for absorption and systemic action are mainly used.

As early as the end of the nineteenth century, spiral organisms were observed in animal stomachs. Although identical observations were made in human biopsy specimens in 1906, it was not until 1975 that the presence of this bacterium was first associated with gastritis. Shortly after this, association of the bacterium with gastritis, peptic ulcers and some forms of gastric cancer were confirmed. The bacterium was eventually named *Helicobacter pylori* (*H. pylori*) and other *Helicobacter* species have since been isolated from animal stomachs giving rise to an entirely new genus. Half of the western population over 60 years old and most of the developing world population is infected with *H. pylori*. Although only a minority of infected people are symptomatic the bacterium is now a well recognised risk factor for gastric cancer so its eradication at the population level is a major goal of modern medicine.

*H. pylori* is a Gram negative bacterium that lives within and under the mucus layer on the surface of the mucosa in the human stomach where it can trigger inflammation. Bacteria were once thought not to be able to colonise this environment due to pH change and mucus shedding. However, *H. pylori* is specifically adapted to this constantly changing environment.

The sequence of events that leads to the establishment of *H. pylori* infection is still only partly understood. The helical shape and the flagellae provide *H. pylori* with high motility even in the viscous gastric environment. Also, segments of lipopolysaccharades of the outer membrane of *H. pylori* have the ability to mimic the Lewis$^x$ and/or Lewis$^y$ blood group antigen, thus camouflaging the bacterium and evading host defences. However, the most important feature of *H. pylori* that allows colonisation and survival in the stomach environment is the high rate of production of the urease enzyme. Urease catalyses the degradation of urea into carbon dioxide and ammonia, and is present both internally and externally (from cell lysis). It was first believed that the ammonia released by external urease (creating a cloud in the immediate surrounding of the bacteria) protected *H. pylori* from acid attack, but, it was later discovered that under acidic conditions the internal urease maintains a tolerable periplasmic pH, allowing protein synthesis and bacterial growth (Scott D et al, The role of internal urease in acid resistance of *Helicobacter pylori*. Gastroenterology, 114:58-70 1998).

*H. pylori* infection causes inflammation of the gastric mucosa (i.e. gastritis) by both directly affecting epithelial cells and by inducing an inflammatory response. The distribution and severity of gastritis varies widely. Most people with *H. pylori* infection are asymptomatic, but symptoms vary from dyspepsia (upper abdominal discomfort with or without nausea, vomiting and burning sensations in the epigastrum) to peptic ulcers and gastric cancer. Duodenal ulcer and gastric cancer seem to be mutually exclusive outcomes of *H. pylori* infection. It is now recognized that antral-predominant *H. pylori* gastritis stimulates increased release of gastrin from the antral mucosa which results in excessive secretion of acid by the parietal cells in the healthy, uninflamed body mucosa. This increased acid secretion results in an increased duodenal acid load and gastric metaplasia of the duodenal bulb. *H. pylori* can colonise this gastric metaplasia, and so the combination of both increased acid load and the colonising organism induce duodenal mucosal damage and ulceration (McColl, *Helicobacter pylori* 1988-1998. European journal of gastroenterology and hepathology, 11:13-16 1999). In contrast, gastritis involving the acid-secreting corpus region of the stomach leads to hyposecretion of gastric acid, eventually leading to achlorhydria, which is associated with an increased risk of gastric cancer (El-Omar et al, Interleukin-1 polymorphisms associated with increased risk of gastric cancer, Nature, 404:398-402 2000). The nature of this relationship is however still unclear.

*H. pylori* strains expressing the vacA gene, responsible for the secretion of the cytotoxin VacA that causes the formation of vacuoles in mammalian cells in vitro, are also associated with more severe pathologies. In addition, the severity of gastric inflammation correlates with cagA gene expression which is responsible for the secretion of the cytotoxin-associated protein CagA that can induce cell death (El-Omar et al., 2000). However, these virulence factors cannot explain the difference in clinical outcome described above, since both duodenal ulcer and gastric cancer are associated with vacA and cagA expression. Host genetic factors, and environmental factors such as diet, may explain the different responses to *H. pylori* infection. Recently, genetic factors affecting the production of interleukin-1-β, an important pro-inflammatory cytokine and a powerful inhibitor of acid secretion, have been implicated in the development of gastric cancer (El-Omar et al, 2000).

The finding that *H. pylori* infection is a marked risk factor for subsequent development of gastric cancer means that infection is rarely now treated conservatively. Eradication of *H. pylori* in infected individuals, whether symptomatic or not, is increasingly common. Antibiotics form the basis of all treatments although neither mono nor dual therapies have ever been especially efficacious. The addition of bismuth compounds or antisecretory drugs to antibiotic dual therapies, forming the commonly used triple therapies, has led to significantly improved eradication rates (typically 70-95%). Quadruple therapies have also been used, consisting of two antibiotics in combination with an acid suppressing agent and a bismuth compound. However, due to their complexity and an undesirable interaction between bismuth and acid suppressing agents, these therapies have been restricted to second line treatment for resistant *H. pylori* infection. Recently, efforts have concentrated on the reduction of doses and duration of therapy to improve compliance, side effects and costs. Nonetheless, we are still left with mass prescription of antibiotics for one of the world's most prevalent infections. As a result antibiotic resistance is becoming increasingly common.

Prior to the discovery of *H. pylori* the main treatment of gastric and peptic ulcers was the administration of inhibitors of acid secretion, namely H2-antagonist and proton pump inhibitors (PPI). Following the establishment of the role of *H. pylori* in such diseases, the addition of antisecretory agents was found to enhance the eradication rates of all the antibiotics.

During antisecretory therapy *H. pylori* tends to migrate from the antrum to the less alkaline corpus which may also favour its eradication. Nevertheless, acid inhibition increases the bioavailability of antibiotics by increasing the pH of the gastric juice, which first increases their concentration and secondly stabilises the active form. In addition, PPI may increase direct delivery of antibiotics to the mucosa by decreasing gastric mucus viscosity in vivo.

In vitro, *H. pylori* is naturally susceptible to most antibiotics but, unfortunately, no single antibiotic therapy achieves high eradication rates in vivo. This could either be due to extrinsic factors (extent of infection, immune status of individuals and compliance with treatment regimens), or intrinsic factors (biochemically and genetically based microbial resistance) (Hoffman, Antibiotic resistance mechanisms of *Helicobacter pylori*, Canadian journal of gastroenterology, 13(3): 243-249 1999).

Antibiotics, which are usually administered orally to eradicate *H. pylori* infection, are predominantly absorbed across the intestinal lumen, and their subsequent gastric secretion is not clearly defined. The availability and stability of antibiotics at the site of infection depends upon their pKa, lipid solubility and complexation by protein, as well as the mucosal pH gradient.

Among the many antibiotics examined in vitro, only four are clinically useful: amoxycillin, tetracycline, the newer macrolides (of which clarithromycin is best studied, although others are under investigation) and nitroimidazoles (usually metronidazole). Clarithromycin, which is less affected by a decrease in pH than that of other compounds, has a very low MIC for *H. pylori* (MIC50, 0.03 mg.L-1). As a monotherapy, clarithromycin eradicates only about 34% of infections which rises to about 70% in combination with metronidazole. In triple therapy with a PPI and either metronidazole or amoxycillin this increases to 85-95% (Hoffman 1999). The frequency of resistance to clarithromycin (i.e. macrolides) varies from country to country and seems to parallel the use of this therapeutic class to treat other infections (mainly respiratory tract infection). Similarly, it is of concern that prescription of clarithromycin for *H. pylori* could lead to resistance of other pathogenic bacteria. A marked difference has also been found between the rates of resistance to nitroimidazoles in developed (10-50%) and developing (80-90%) countries, related to their extent of use in other infections such as parasitic, genital, and dental infections.

Resistance to these antibiotics significantly affects their efficacy in bacterial eradication. However, Clarithromycin resistance, for example, alters the efficacy of antisecretory based triple therapy with amoxicillin and clarithromycin, eradication changing from 94% (susceptible) to 45% (resistant). There has not been any report of resistance to the β-lactam amoxycillin in *H. pylori* infection but *H. pylori* strains have been described that repeatedly showed higher MIC (0.25 or 0.5 mg. L-1 instead of usually ≦0.03 mg.L-1). One of the four penicillin-binding proteins that are normally present in susceptible strains was missing in isolates with higher MICs. Currently, this phenomenon seems rare, but it nevertheless indicates the need for surveillance.

Antibiotic resistance may also be linked to compliance because, when a patient takes a course of drugs incompletely, there is the possibility that the concentration of antibiotic at the site of infection decreases to a level where resistance emerges; an increase in resistance is then anticipated.

Toxic metal compounds have been in use for some considerable time in the treatment of gastrointestinal symptoms and of gastrointestinal and even systemic infections, but significant side effects occur, such as the encephalopathy seen with bismuth complexes (Gorbach S. L., *Gastrenterology*, 99: 863-875 (1990)). Newer "Colloidal" bismuth compounds such as De-Noltab™ (bismuth sub-citrate) and Pepto-Bismol™ (bismuth sub-salicylate) are less well absorbed in man and have some activity against gastrointestinal bacteria. However, it has still been shown that significant and prolonged plasma levels of bismuth are found following ingestion of such colloidal preparations (Nwokolo et al, *Alimentary, Pharmacology and Therapeutics*, 4:163-169 (1990)) (reaching up to 135 μg/l for De-Noltab™ and 5 μg/l for Pepto Bismol™).

These earlier metal-based therapies in the gastrointestinal tract have, unknowingly, been mainly effective against gastrointestinal pathogens due to their synergistic action with conventional antibiotics, rather than due to any significant antimicrobial properties per se, as unlike in vitro, sufficient concentrations of bismuth may not reach the bacteria in vivo.

This has been suggested by work we have carried out on the therapeutic role of bismuth compounds in the eradication of *H. pylori*.

The microbial infections treatable by the methods described herein relate to *H. pylori*. *H. pylori* is a Gram negative bacteria that has been strongly implicated in chronic active gastritis and peptic ulcer disease (Marshall et al, *Medical Journal of Australia*, 142:439-444 (1985); Buck, G. E., *Journal of Clinical Microbiology*, 3:1-12 (1990)). More recently, it has also been implicated in the development of gastric cancer and lymphoma. As mentioned above, *H. pylori* infection is one example where complex triple therapies are required for eradication. One example is based on Lansoprazole™ (30 mg b.d.) with amoxicillin (1000 mg b.d.) and metronidazole (400 mg t.d.s.). It would be particularly useful therefore to have available a simpler, less expensive therapy with good eradication rates. In particular, it would be useful to produce an anti-*H. pylori* agent that negates the use of systemic antibiotics and reserves these for use against more serious (life-threatening) bacterial infections.

*H. pylori* requires nickel ions for the assembly of active urease. However, nickel is a rare trace metal in the diet and is poorly absorbed. Therefore, its concentration in human blood and mucosa is very low (2-11 nM). Due to the high requirement of *H. pylori* for this metal ion, metal homeostasis is crucial for its survival in the gastric environment. The availability of the complete DNA sequence of the *H. pylori* genome has revealed the presence of multiple putative ion-binding proteins and membrane transporters for divalent cations (Fulkerson et al, Conserved residues and motifs in the NixA protein of *Helicobacter pylori* are critical for the high affinity transport of nickel ions, *The Journal of Biological Chemistry*, 273(1):235-241 1998). Nickel and other cations are imported by a relatively non-specific transport protein, namely NixA, which allows maximal accumulation of trace metals. However, these cations are enzyme inhibitors and urease is particularly sensitive to certain cations (Perez-Perez et al., Effects of cations on *Helicobacter pylori* urease activity, release, and stability, *Infection and immunity*, 62(1):299-302 1994). Therefore, the intracellular concentration of cations is regulated in *H. pylori* by specific membrane proteins, namely CopA, CopA2 and CadA, that clear copper, cadmium and zinc from the cytoplasm, and to a lesser extent cobalt (Herrmann et al., *Helicobacter pylori* CadA encodes an essential Cd(II)-Zn(II)-Co(II) resistance factor influencing urease activity. *Molecular microbiology*, 33(3):524-5361999).

The use of dietary metals to treat gastrointestinal infections is disclosed in WO 98/16248. The dietary metals are used in the form of complexes with ligands such as citrate, maltol, lawsone and tropolone.

Perez-Perez et al, mentioned above, teaches only the decrease in urease release caused by metal cations and, although specific therapies are postulated, the document teaches that ions other than $Ca^{2+}$ and $Mg^{2+}$ are non-specific.

EP-A-0770391 describes the use of a wide range of metals for the treatment of a wide range of different medical conditions. There is no mention of selective treatment of *H. pylori* or of which metal ions would be useful for this purpose.

WO 98/10773 describes the use of zinc or cobalt hyaluronate as antimicrobial agents. The polymeric, high molecular weight hyaluronic acid component is suggested as being essential for the pharmacological activity and the data show that the compounds have no selectivity, being active against a wide range of different microorganisms.

Mobley et al, *Helicobacter*, Volume 4, Nov. 3, 1999, pages 162 to 169 describe a mechanistic investigation into the effect of bismuth, $Ni^{2+}$, $Zn^{2+}$, $Cu^{2+}$ and $Co^{2+}$ on Hpn-negative mutants of *H. pylori*. Hpn was found to have no effect on $Co^{2+}$ tolerance in this academic study and no selectivity was attributed to any of the metals. The reference does not suggest anything other than conventional bismuth salt treatments for infections with *H. pylori*. The teaching of the document is away from Zn, Cu and Co, particularly so far as selectivity is concerned. Furthermore, there is nothing in Mobley et al that would suggest that cobalt has activity at about pH4 which is the pH in the environment for *H. pylori* in vivo.

There exists a need for treatments of gastrointestinal infections which are selective for the bacteria causing the infection and which do not adversely interfere with other bacteria present in the gut.

It has now been found that cobalt salts can be used to treat gastrointestinal infections with good selectivity. Surprisingly, cobalt shows excellent selectivity for *H. pylori* compared to other microorganisms.

Accordingly, the present invention provides the use of a cobalt salt in the manufacture of a medicament for selectively treating and/or preventing a gastrointestinal infection caused by *H. pylori*. Also provided by the invention is a method of selectively treating and/or preventing a gastrointestinal infection caused by *H. pylori* in a mammal which comprises the step of administering to a subject a therapeutically effective amount of a cobalt salt.

Cobalt salts have been found to be particularly effective against *H. pylori* and especially selective for *H. pylori* ie, leaving many other beneficial bacteria present in the gut unaffected by the treatment. Thus, the invention is directed to the selective targeting of *H. pylori* infections.

The cobalt salt is preferably a cobalt (II) salt since it is well-known that cobalt (II) salts are readily available unlike cobalt (III) salts, and because there is concern over the long term safety of cobalt (III) salts.

The cobalt salt must be capable of providing cobalt ions (in hydrated form) at the site of the infection. It has been found that strongly complexing ligands such as EDTA can bind the cobalt ion so strongly that activity against the bacteria causing the infection is inhibited. Therefore, it is preferred that the cobalt salt comprises an anion which does not complex too strongly with the cobalt ion. In addition, this will facilitate delivery of the cobalt ion to, and binding by, the mucus layer. This is preferred as the gastric mucus layer is the environment where *H. pylori* is resident. Preferably the anion is the anion of a strong acid (ie, having a pKa of less than about 4) and/or is monovalent. However, anions of weaker acids such as the amino acids, for example methionine and cysteine, may also be employed. Suitable anions, which must be substantially non-toxic and are preferably non-polymeric (ie, have a molecular weight of less than about 1000 daltons, preferably less than 500 daltons, more preferably less than 200 daltons), include chloride, nitrate, sulphate, phosphate, carbonate, hydroxide, acetate and mixtures thereof (including salts containing two or more anions). Of these, chloride, carbonate, hydroxide and acetate are more preferred. Cobalt carbonate and hydroxide have the advantage of being substantially insoluble in aqueous media at higher pH values but of forming soluble salts at lower pH values. Thus, these latter two salts can have the advantage of gradually delivering the cobalt ions at the site of infection which is generally in an environment where the pH is low. This could increase the residence time of the cobalt (II) ion in the gastric environment.

The cobalt salts of the invention preferably deliver cobalt ions in uncomplexed form (ie, such that $Co(H_2O)_6^{2+}$ ions are formed when the salt is in aqueous solution under gastric conditions, for example) or in the form of complexes in which the cobalt ion is relatively weakly bound such that the complex at least partly dissociates to provide cobalt ions in a form suitable for uptake into *H. pylori* at the site of infection. Thus, it is preferred that the anion in the cobalt salt and any ligand present in the salt or in the compositions of the invention does not bind to cobalt so strongly that cobalt ions (such as in hydrated form) are not available or are only available in relatively low amounts at the site of the infection. In one embodiment, the invention is carried out in the absence of a bi- or poly-dentate complexing ligand for the cobalt ions. Alternatively or additionally, the cobalt salt is preferably the sole di- or polyvalent metal species used in the invention. Preferably, the cobalt salt provides $Co(H_2O)_6^{2+}$ ions as the major species (ie, the cobalt present as $Co(H_2O)_6^{2+}$ ions is present in an amount of at least 50% by weight based on the total amount of cobalt) when the salt is dissolved in excess deionised water (eg, greater then 10 molar excess, preferably greater than 100 molar excess) at 25° C. Alternatively, or additionally, the cobalt ion/ligand complex preferably has an apparent affinity constant $K_{app}$ of less than 6, more preferably less than 5, wherein $K_{app}$ is calculated at pH7 and 25° C. and is defined by the formula:

$$\log K_{app} = \log K_i - \log\left(\frac{[H^+]}{K_{a1}} + \frac{[H^+]^2}{K_{a1}K_{a2}} + \ldots\right)$$

where $K_i$ is the stability of the species I formed between the ligand and metal, and $K_{an}$ are the different acid dissociation constants of the ligand.

It will be appreciated that whether a ligand binds strongly to cobalt, in the context of the invention, will depend on thermodynamic and kinetic factors. Thus, anions forming complexes with cobalt with high affinity may still be suitable for use in the invention if the cobalt ion is kinetically labile. On the other hand, complexes of lower affinity may be unsuitable for use in the invention if the kinetics of the dissociation are too slow. The ability of a given complex to provide a sufficient amount of cobalt ions in vivo can be readily determined by those skilled in the art on the basis of simple tests.

The present invention has the advantage of targeting the mucus layer with the cobalt ion which may not occur with strongly bound cobalt complexes that would by-pass or not interact with the mucus layer. The mucus layer harbours *H. pylori* in the stomach. Also, the pH gradient within the mucus layer may facilitate the transfer of cobalt ions through this layer to the bacteria. The cobalt ions may be used together with one or more agents which facilitate targeting to the mucus layer. For example, the cobalt salt may be used together with agents such as those selected from the group consisting of muco-adhesives and mucilagenous agents (e.g. acacia gum, tragacanth gum and methyl cellulose), antimuscarinic agents (such as pirenzapine which binds to the gastrointestinal mucosa and delays gastric emptying), mucolytic agents (such as acetylcysteine, guaiphenesin or ammonium citrate), anti-gastritis agents and anti-ulcer agents which target the gastric mucus (such as carbenoxolone).

Currently, the most preferred anion is chloride and the preferred cobalt salt is cobalt (II) chloride, optionally hydrated eg, $CoCl_2.6H_2O$.

The cobalt salts may comprise, or may be administered together with, a neutral or anionic ligand, although this is less preferred. The ligands may be useful in selectively delivering the cobalt ions to the site of infection. Suitable ligands include cysteine, methionine, and mixtures thereof.

The cobalt salts may also be used together with one or more ferric, zinc or bismuth compounds or mixtures thereof. Suitable ferric compounds include, for example, ferric maltol. Suitable zinc compounds include zinc citrate.

The cobalt salt, which may be a mixture of two or more different cobalt salts, may be administered rectally or orally, preferably orally. The salt may be in the form of a liquid formulation, such as an aqueous solution, a suspension or an emulsion, for example, or it may be in the form of a solid formulation, such as a capsule, pill or powder, for example. The formulations containing the cobalt salt may contain pharmaceutically acceptable excipients, diluents, carriers or other additives.

By "pharmaceutically acceptable" we include the normal meaning that the carriers must be "acceptable" in the sense of being compatible with the active ingredient (complex) and not deleterious to the recipients thereof.

The composition may be in the form of a solid or liquid. Suitable solid carriers include starch, lactose, dextrin and magnesium stearate. Liquid carriers should be sterile and pyrogen free: examples are saline and water.

Liquid formulations of the cobalt salts are particularly suitable for oral administration.

The cobalt salts may be formulated with a physiologically acceptable diluent or carrier for use as pharmaceuticals for veterinary or human use in a variety of ways. However, compositions in which the diluent or carrier is other than a non-sterile solution in water are generally preferred. Oral administration is, however, more generally to be preferred for the treatment of *H. pylori* infections in humans and the complexes of the present invention may be given by such a route. For oral administration in humans, it is more usual to use compositions incorporating a solid carrier, for example starch, lactose, dextrin or magnesium stearate. Such solid compositions may conveniently be shaped, for example in the form of tablets, capsules (including spansules), etc. However, liquid preparations are especially useful for oral administration to patients who have difficulty in swallowing solid forms.

Preferably, the amount of cobalt salt which is required for the treatment of gastrointestinal infections according to the invention varies from <1 to 300 mg, more preferably 1-100 mg, such as 1-50 mg of cobalt per day. Single doses may be 1-50 mg, more preferably 1 to 30 mg per day, such as 20 mg per day, for example; doses in formulations which are adapted for delayed or controlled release of cobalt ions may be higher than this, as will be appreciated by the skilled person. A suitable dosage form comprises 10 mg of cobalt and such a dosage will typically be administered twice daily for several weeks (eg 1 to 4 weeks) in order to treat the infection. It will be appreciated by those skilled in the art that other dosage regimens may be equally applicable in the method of the invention.

Advantageously, the cobalt salts are formulated in a composition together with an antibiotic and a pharmaceutically acceptable diluent or carrier. Therefore, in a further embodiment, the present invention provides a pharmaceutical composition for use in the treatment of gastrointestinal infections which comprises a cobalt salt and an antibiotic together with a pharmaceutically acceptable diluent or carrier. Preferably, the composition also comprises a proton pump inhibitor.

Another composition of the invention for use in the treatment and/or prevention of gastrointestinal infections comprises a cobalt salt and a proton pump inhibitor together with a pharmaceutically acceptable diluent or carrier.

The compositions of the invention may comprise a mixture of the cobalt salt and the other pharmaceutically active substance or substances which it contains (such as the antibiotic, for example). Alternatively, the cobalt salt and the other active substance or substances may be kept separate from each other in the compositions and may even be packaged together but designed to be administered separately from each other. Therefore, the compositions of the invention may be in the form of a kit of parts.

The compositions of the invention may comprise more than one antibiotic and/or more than one proton pump inhibitor.

Compositions for treating gastrointestinal infections containing a metal salt, an antibiotic and a proton pump inhibitor, in so-called "triple therapy" methods are known. Antibiotics and proton pump inhibitors, which are conventionally used in these compositions are suitable for use in the compositions of the present invention, provided that they are formulated in such a way as to be compatible with the cobalt salt. Suitable antibiotics include amoxycillin, metronidazole, clarithromycin and mixtures thereof, for example. Suitable proton pump inhibitors include lansoprazole, omeprazole, pantoprazole and rabeprazole for example. Proton pump inhibitors may be replaced by $H_2$ receptor antagonists, such as ranitidine and cimetidine, for example, in the present invention.

The compositions of the invention are preferably used for the selective treatment of gastrointestinal infection with *H. pylori*. Surprisingly, compositions containing cobalt salts are far more toxic for *H. pylori* than other bacteria tested including those of the intestinal tract and both Gram positive and Gram negative bacteria. This is an especially important finding given that one worrying side effect of present antibacterial treatments for *H. pylori* is the eradication of commensal pro-biotic organisms of the gut leading to changes in normal intestinal flora with pathological implications such as antibiotic-induced colitis. Without wishing to be bound by theory, it is believed that the selectivity of cobalt for *H. pylori* may be due to the accumulation of cobalt ions within *H. pylori* and the consequent action of cobalt as a cumulative toxin. For this reason, it can be advantageous to provide cobalt in the form of a controlled release formulation.

Cobalt salts also have the advantage of being selective for *H. pylori* at about pH 4 (eg, pH 3 to 5), which is pH in the environment of *H. pylori* in vivo.

Preferably, the cobalt salts have a selectivity for *H. pylori* such that the ratio of the MIC for cobalt against *H. pylori* to the MIC against other bacteria commonly present in the intestinal tract, for example Gram negative bacteria such as *E. coli*, is preferably greater than 10:1, more preferably greater than 100:1, most preferably greater than 200:1. MIC values are determined by the method described herein in the examples section.

Therefore, the compositions of the invention and other medicaments for use in the method of the invention may be adapted for delayed release of the cobalt ions. Suitable delayed release formulations (also termed controlled release formulations) are well-known to those skilled in the art. The delayed release of cobalt ions may be continuous and/or in the form of pulses. Preferably, the compositions release cobalt ions over a period of from 1 to 10 hours (e.g. from 3 to 10 hours, more preferably 4 to 7 hours).

Controlled release of cobalt ions in the present invention may be achieved in a number of different ways. For example, the cobalt salt may be formulated with a substance which delays gastric emptying. Suitable substances which delay gastric emptying include materials that bind to the gastric mucosa (eg, aluminium compounds such as aluminium hydroxide or sucralfate, the hydrous basic aluminium salt of sucrose octasulphate). Other substances that delay gastric emptying include antispasmodics or anticholinergic agents such as propantheline and atropine. Substances which increase the viscosity of the formulation, eg, polysaccharide polymers such as alginate, may also be used to delay gastric emptying.

Alternatively, controlled release formulations may be derived by providing a formulation that is capable of swelling on contact with water. Thus, the formulation may comprise a cobalt salt together with a polymer capable of forming a polymeric hydrogel, preferably as a coating around the cobalt salt (and any other excipients). Such coatings can be formed, for example, from an anhydride copolymer, a cross-linking agent (eg, oxyethylene sorbitan monolaurate) and a plasticiser (eg, glyceryl triacetate). Styrene-maleic anhydride copolymers and poly(methylvinylether/maleic anhydride) are suitable polymers. The polymer may be applied, for example, as a 1-20% (preferably 8-10%) by weight solution in a solvent mixture of ethylacetate and acetone (preferably about 65:35). Coating may be carried out, for example, by immersion or spraying.

Other systems for controlled release of cobalt may also be used in the invention. Suitable systems include coated beads, tablets with cores comprising microcrystalline cellulose, capsules comprising granules having different release characteristics, multiple layer tablets, porous inert carriers, ion exchange resins and liquid gel preparations.

As described above, it is preferred that the cobalt in the cobalt salts of the invention is in the cobalt (II) form. However, other forms of cobalt may be employed, particularly if they may be converted to the cobalt (II) form at the site of the infection.

In the invention, it has been found that cobalt salts, such as cobaltous chloride, have antibacterial activity, at low concentrations, and are relatively specific to the *H. pylori* genus and that cobaltous ions ($Co^{2+}$) are the active species. Surprisingly, cobalt has been found to be active even against the *H. pylori* strain deprived of its urease enzyme.

Cobalt specifically interferes with the oxidative mechanisms of mammalian tissues and bacteria, which is an activity that is decreased by the addition of cysteine (Orten and Bucciero, The effect of cysteine, histidine and methionine on the production of polycythemia by cobalt. *Journal of biological chemistry*, 176:961-968, 1948). Therefore, in the present invention, the cobalt salt may be used together with the weakly complexing amino acids cysteine and/or methionine.

The presence of cysteine and/or methionine at a weight ratio of 1:5 (cobalt:cysteine and/or methionine) has been found not to affect the MIC of cobalt against *H. pylori* and, therefore, the weight ratio of cysteine and/or methionine to cobalt salt may range from 100:1 to 1:100 (such as 50:1 to 1:50, more preferably 10:1 to 1:10).

Surprisingly, by measuring the MIC of cobaltous ion against *H. pylori*, it has been found that the metal was not only bacteriostatic (i.e. inhibitory of growth), but also bactericidal (i.e. rapidly decreasing viability).

The invention will now be described, by way of illustration only, with reference to the following non-limiting examples. In the examples and throughout the specification all percentages are by weight unless otherwise indicated.

EXAMPLES

Methods

Solutions of metal salts were prepared by dilution of the metal salt, optionally together with the ligand, in ultra-high-purity water. The pH values were adjusted to 7 with concentrated sodium hydroxide. The solutions were γ irradiated for 20 to 30 minutes for sterilisation, and then diluted ten fold in the bacterial growth medium to be used.

A gradient of concentration was obtained by two fold serial dilutions of the medium. The concentrations of metals were analysed by inductively coupled plasma spectrometry. Each dilution was inoculated with the different bacteria to be tested, by multi-point inoculating on the agar media, or suspending in the broth media.

Media were incubated for *Helicobacter pylori* in a microaerobic atmosphere (gas jar containing a CampyGen® pack, 5% $O_2$-10% $CO_2$-85% $N_2$ by volume) with constant shaking (orbital shaker, 140 rpm) at 37° C. for five days.

The presence or absence of bacterial growth was reported within the concentration gradient and the minimum concentration of complex in the medium that inhibits totally the bacterial growth (MIC) was determined. The growth on an agar plate was detected by the presence of colonies, and by turbidity in the broth media. The bacteria were identified by the Gram morphology test. *Helicobacter pylori* growth was also confirmed by biochemical test on the catalase, urease and oxidase activity.

Media and Bacteria Used:

| Media | Bacteria Gram − | Bacteria Gram + |
|---|---|---|
| BHI<br>Brain-Heart infusion<br>+2% horse serum<br>Agar and Broth | *Helicobacter pylori* | |
| MH<br>Mueller-Hinton<br>+2% horse serum<br>Agar and Broth | *Helicobacter pylori*<br>*Echerichia coli*<br>*Pseudomonas aeruginosa*<br>*Klebsiella* | *Staphylococcus aureus*<br>*Enterococcus faecalis*<br>*Enterococcus faecium*<br>Coagulase negative<br>Staphylococcus |
| ISO<br>Isosensitest<br>+5% horse blood<br>in Agar | *Helicobacter pylori*<br>*Echerichia coli*<br>*Pseudomonas aeruginosa* | *Staphylococcus aureus*<br>*Enterococcus faecalis*<br>*Enterococcus faecium* |
| +2% horse serum<br>in Broth | *Klebsiella* | Coagulase negative<br>Staphilococcus |
| R&P<br>Reynolds and Penn<br>defined medium for *H. pylori* Broth | *Helicobacter pylori* | |

-continued

| Media | Bacteria Gram – | Bacteria Gram + |
|---|---|---|
| STH<br>St Thomas' Hospital<br>Fully defined medium<br>for<br>H. pylori<br>Broth at pH4 or 7 | Helicobacter pylori | |

FIG. 1 is a graph showing the inhibition of *H. pylori* growth by cobalt (cobaltous chloride) in the STH medium.

Example 1

Selectivity of Cobalt for *Helicobacter pylori*

Cobalt ion in the oxidation state +2 ($Co^{2+}$) as cobalt chloride was found to inhibit the growth of *Helicobacter pylori*, in vitro, with a minimum inhibitory concentration (MIC) of 0.06 mg/l.

The activity of $Co^{2+}$ was specific for *Helicobacter pylori* (Table 1). The activity of $Co^{2+}$ as cobalt chloride against other bacteria was higher than the estimate limit between active and non-active metals, i.e. 32 mg/l.

TABLE 1

MIC of cobalt chloride against other bacteria on Mueller-Hinton agar with 2% horse serum and isosensitest agar with 5% horse blood. Several strains of each genus were tested.

| Bacteria | MIC (mg/l) |
|---|---|
| Gram positive bacteria | |
| *Staphylococcus aureus*<br>Coagulase negative staphylococcus<br>*Enterococcus faecalis*<br>*Enterococcus faecium* | >32 |
| Gram negative bacteria | |
| *Pseudomonas aeruginosa*<br>Klebsiella<br>*Echerichia coli* | >32 |

Example 2

Activity of Cobalt Relative to Other Metal Ions

Other metal salts were tested for their action against *H. pylori*, and were found to be poorly active (Table 2) with the exception of bismuth, which was active, but only at much higher levels than cobalt (II). This suggests a specific sensitivity of *H. pylori* to $Co^{2+}$ compared to other metals.

TABLE 2

MIC of metal ions against *H. pylori* on STH broth (NCTC 11637 and seven clinical isolates)

| metal ion tested | MIC (mg/l) |
|---|---|
| metal chloride: | |
| $Fe^{3+}$ | >32 |
| $Zn^{2+}$ | >32 |
| $Mn^{2+}$ | >32 |
| $Cu^{2+}$ | 16-32 |
| $Ni^{2+}$ | >32 |

TABLE 2-continued

MIC of metal ions against *H. pylori* on STH broth (NCTC 11637 and seven clinical isolates)

| metal ion tested | MIC (mg/l) |
|---|---|
| $Co^{2+}$ | 0.03-0.6 (median 0.06) |
| others: | |
| $V^{4+}$ (vanadyl sulfate) | >32 |
| $Cr^{2+}$ (chromium nitrate) | >32 |
| $Mo^{6+}$ (molybdenum oxide) | >32 |
| $Bi^{3+}$ (bismuth nitrate) | 4-8 |

Examples 3 to 12

Activity of Different Cobalt Salts

The MIC (mg/l) of different cobalt salts for *H. pylori* was determined at two different pH values. The results are given in Table 3.

TABLE 3

MIC of different cobalt salts (Co (II) unless otherwise indicated)

| Cobalt (Co) Salt | pH 4-7* | pH 7 |
|---|---|---|
| Co chloride | 0.03-0.4 | 0.06-0.4 |
| Co nitrate | 0.06 | 1 |
| Co carbonate | 0.03-0.125 | 0.125-1 |
| Co bromide | 0.06-0.125 | 1-4 |
| Co hydroxide | 0.125 | 2-4 |
| Co acetate | 0.125 | 0.5-2 |
| Co phosphate | 4 | 0.8 |
| Co sulfate | 1 | 25 |
| Co fluoride | <5.4 | 9.5-1.9 |
| Co (III) fluoride | <4.5 | 15 |

*pH4-7 indicates that the pH of the media changes during the experiment as the bacteria neutralise the starting acidic environment. This mimics better, therefore, the physiological situation where an ion may traverse the gastric mucus layer from an acidic pH to a neutral pH.

Example 13

Effect of Ligands on the Activity of Cobalt

The addition of the following ligands was found not to impair the MIC of cobalt against *H. pylori*, although some more strongly complexing ligands may have reduced selectivity:

| | |
|---|---|
| cysteine | acetohydroxamic acid |
| methionine | alanine Hx |
| maltol | β-alanine Hx |
| ethylmaltol | glutamine Hx |
| lawsone | phenylalanine Hx |
| deferiprone | |

(Hx = hydroxamate of the amino acid)

The strongly complexing ligands EDTA and folate inhibited the action of cobalt against *H. pylori* and the strongly bound cobalt complex of Vitamin $B_{12}$ exhibited greatly reduced activity against *H. pylori*.

Example 14

Action of cobalt (cobaltous chloride) (Co) and amoxycillin (Ax) against *Helicobacter pylori*

|  | 0 | 0.002 | 0.004 | 0.008 | 0.015 | 0.03 | 0.06 mg/l Ax |
|---|---|---|---|---|---|---|---|
| 0 | + (control) | + | + | + | + | + | − |
| 0.004 | + | + | + | + | + | + | − |
| 0.008 | + | + | + | + | + | + | − |
| 0.0015 | + | + | + | + | + | + | − |
| 0.030 | − | − | − | − | − | − | − |
| 0.060 | − | − | − | − | − | − | − |
| 0.120 | − | − | − | − | − | − | − |
| mg/l Co | | | | | | | |

(+) = growth in the medium
(−) = inhibition of growth
MIC of cobalt (no amoxycillin): 0.030 mg/l
MIC of amoxycillin (no cobalt): 0.06 mg/l The combination of cobalt with the antibiotic amoxycillin does not impair the action of cobalt or amoxycillin against *Helicobacter pylori*. The MIC values are unchanged.

Example 15

Inhibition of *Helicobacter pylori* Growth by Cobalt (Cobaltous Chloride) in the STH Medium FIG. 1 shows the results of this experiment as cfu/ml plotted against time (hours).
$I_{50}$=inhibition of 50% of the *Helicobacter pylori* inoculated by cobaltous chloride. Concentration of cobalt in the medium was 2.00 ppm.
Cobalt total inhibition is achieved in 8 hours and the cobalt $I_{50}$ level is reached after 5 hours.

Example 16

The following is an example of a formulation for use according to the invention:

| $CoCl_2 \cdot 6H_2O$ | 100 mg |
|---|---|
| Alginic acid | 200 mg |
| Sucrose | 500 mg |
| $Al_2O_3$ | 5 ml of 4% w/w water suspension in peppermint water |

15 mg propantheline may be included in the formulation as an antispasmodic.

Example 17

The following is an example of a formulation for use according to the invention:

| $CoCl_2 \cdot 6H_2O$ | 100 mg |
|---|---|
| Microcrystalline cellulose | 400 mg |
| Hypromellose | qv |
| Hypromellose phthalate | Coating |

Example 18

The following is an example of a formulation for use according to the invention:

| $CoCO_3$ | 40 mg as cobalt |
|---|---|
| Sulfacrate | 1 g |
| Minors | qv |

For dosing at 1-2 g every 4 hours.

Example 19

The data below indicate the selectivity of cobalt ions for *H. pylori* (Tables 4 and 5). In addition it should be noted that in Table 5 the activity of cobalt against *H. pylori* is about 10 fold greater at pH 4 than pH 7. Most anti-microbials are less active at acidic pH so such a finding is not necessarily to be expected.

TABLE 4

MIC and Selectivity Ratio of Metal Salts against Pathogenic Micro-organisms

|  | H. pylori | Klebsiella | E. coli | Pseudomonas aeruginosa | Ent faecalis | Staphylococcus (aureus or Oxford Staph) | Average Selectivity Ratio |
|---|---|---|---|---|---|---|---|
| Cu | 24 (16/32) | >32 | >32 17.15[a] | >32 1.75[a] | >32 | >32 17.15[a] | 1.02 |
| Zn | >32/32 | >32 | >32 17[a] | >32 1.7[a] | >32 | >32 17[a] | 0.76 |
| Fe | >32/>32 | >32 | >32 | >32 | >32 | >32 | 1.00 |
| Mn | >32/>32 | >32 | >32 | >32 | >32 | >32 | 1.00 |
| Ni | >32/>32 | >32 | >32 22.89[a] | >32 22.89[a] | >32 | >32 22.89[a] | 0.89 |
| Co | 0.06 (<0.03-0.125) | >32 | >32 22.97[a] | >32 2.3[a] | >32 | >32 22.97[a] | 434 |

TABLE 4-continued

MIC and Selectivity Ratio of Metal Salts against Pathogenic Micro-organisms

|  | H. pylori | Klebsiella | E. coli | Pseudomonas aeruginosa | Ent faecalis | Staphylococcus (aureus or Oxford Staph) | Average Selectivity Ratio |
|---|---|---|---|---|---|---|---|
| Ag | 0.13 (<0.06-0.2) | — | 0.11[a] | 0.11[a] | — | 0.11[a] | 0.85 |

Footnotes to Table 4:
[a]MIC results extrapolated from bacterial survival rates of organisms cultured in protein broth and then transferred to phosphate-buffered saline. From: Zhao, Z H., Sakagami, Y., and Osaka, T. Relationship between residual metal ions in a solution and the inhibitory capability of the metal ions for pathogenic bacterial growth. Bulletin of the Chemical Society of Japan 71(4): 939-945; 1998. It should be noted that accurate comparisonsbetween MIC results of different laboratories are difficult because conditions are not exactly replicated. However, these data of Zhao, et al are from experiments with liquid cultures rather than solid (agar) plates making conditions closer to those reported in the method described here-in. Indeed, the relative similarity between the two groups for MIC data of most metals against most organisms supports the use of this data for comparison.
Average selectivity ratio = (Sum of MIC values against all bacteria except H. pylori ÷ No. of MIC values) ÷ MIC value for H. pylori.

TABLE 5

MIC of Cobalt salts against H. Pylori at pH 4 and pH 7

| Co compound | Strain 1 (pH 4) | Strain 1 (pH 7) | Strain 2 (pH 4) | Strain 2 (pH 7) | Mean ratio pH 4:pH 7 |
|---|---|---|---|---|---|
| Chloride | 0.015 | 0.03/0.125 | — | — | 0.5 & 0.12 |
| Nitrate | 0.05 | 0.69 | 0.055 | >0.69 | 0.07 & 0.08 |
| Carbonate | 0.09 | 1.09 | <0.02 | 1.09 | 0.048 & 0.018 |
| Bromide | <0.04 | 1.12 | 0.09 | 4.49 | 0.036 & 0.02 |
| Hydroxide | 0.11 | 1.9 | 0.11 | 3.80 | 0.058 & 0.029 |
| Acetate | 0.11 | 2.03 | 0.11 | 1.01 | 0.054 & 0.11 |

Mean ratio of results at pH 4 against results at pH 7 is 0.095, suggesting that at pH 4 the efficacy of the cobalt ion is an order of magnitude more efficacious than at pH 7

Example 20

In a tolerance study, six patients with *H. pylori* infection ingested a low dose of 20 mg/day cobalt, as cobalt chloride (10 mg b.d), for two weeks. There were no reported adverse effects. In one patient the cobalt was taken also with a proton pump inhibitor (Lansoprazole) while the remaining 5 took cobalt alone as capsules (4 patients) or a solution (1 patient). 3 of these patients had gastritis and/or duodenitis with a duodenal ulcer also in one of these three. The other 3 had oesophagitis and/or normal stomach and duodenum.

The invention claimed is:

1. A method of selectively treating a gastrointestinal infection caused by *Helicobacter pylori* (*H. pylori*) in a mammal, which comprises the step of administering to a mammal a therapeutically effective amount of a cobalt salt comprising an anion of an acid having a pKa of less than about 4 and/or which is monovalent, wherein the cobalt salt is selective for *H. pylori* at a pH of 3 to 5 and wherein the cobalt salt delivers cobalt ions in an uncomplexed form and wherein a therapeutic amount of the cobalt salt selectively targets *H. pylori* infections.

2. The method of claim 1, wherein the cobalt salt is a cobalt (II) salt.

3. The method of claim 2, wherein the cobalt salt is administered together with a proton pump inhibitor.

4. The method of claim 1, wherein the cobalt salt is administered together with a proton pump inhibitor.

5. The method of claim 1, wherein the cobalt salt is bactericidal for *H. pylori*.

6. The method of claim 1, wherein the anion is selected from chloride, nitrate, sulphate, phosphate, carbonate, hydroxide, acetate and mixtures thereof.

7. The method of claim 6, wherein the anion is chloride.

8. The method of claim 7, wherein the cobalt salt is hydrated cobalt chloride.

9. The method of claim 1, wherein the composition further comprises one or more agents selected from the group consisting of muco-adhesives, mucilaginous agents, antimuscarinic agents and mucolytic agents.

10. The method of claim 1, wherein the cobalt salt is selective for *H. pylori* such that it is more toxic for *H. pylori* than other bacteria present in the gut, wherein the bacteria are selected from the group consisting of *Klebsiella*, coagulase negative *staphylococcus*, *Enterococcus faecalis*, *Enterococcus faecium*, and *Escherichia coli*.

11. The method of claim 10, wherein the bacteria are *Klebsiella*, coagulase negative *staphylococcus*, *Enterococcus faecalis*, and *Enterococcus faecium*.

12. The method of claim 1, wherein the ratio of minimum inhibitory concentration for the cobalt salt against *H. pylori* to the minimum inhibitory concentration of the cobalt salt against other bacteria normally present in the intestinal tract of mammals is greater than 10:1.

13. The method of claim 1, wherein the amount of cobalt salt provides 1 to 100 mg of cobalt per day.

14. The method of claim 1, wherein the cobalt salt is more toxic to *H. pylori* as compared to other bacteria in the gut.

15. A method of selectively treating a gastrointestinal infection caused by *Helicobacter pylori* (*H. pylori*) in a mammal, which comprises the step of administering to a mammal a therapeutically effective amount of a pharmaceutical composition comprising a cobalt salt comprising an anion of an acid having a pKa of less than about 4 and/or which is monovalent and which is adapted for the delayed release of cobalt ions over a period within the range of 1 to 10 hours, wherein the cobalt salt is selective for *H. pylori* at a pH of 3 to 5 and wherein the cobalt salt delivers cobalt ions in an uncomplexed form and wherein a therapeutic amount of the cobalt salt selectively targets *H. pylori* infections.

16. The method of claim 15, wherein the composition further comprises a proton pump inhibitor, or an $H_2$ receptor antagonist.

17. The method of claim 15, wherein the cobalt salt is a cobalt (II) salt.

18. The method of claim 17, wherein the cobalt salt comprises an anion selected from chloride, nitrate, sulphate, phosphate, carbonate, hydroxide, acetate and mixtures thereof.

19. The method of claim 18, wherein the anion is chloride.

20. The method of claim 15, wherein the cobalt salt is selective for *H. pylori* such that it is more toxic for *H. pylori* than other bacteria present in the gut, wherein the bacteria are selected from the group consisting of *Klebsiella*, coagulase negative *staphylococcus, Enterococcus faecalis, Enterococcus faecium*, and *Escherichia coli enterococcus, enterococcus faecium* and *Echerichia coli*.

21. The method of claim 20, wherein the bacteria are *Klebsiella*, coagulase negative *staphylococcus, Enterococcus faecalis*, and *Enterococcus faecium*.

22. The method of claim 15, wherein the ratio of minimum inhibitory concentration for the cobalt salt against *H. pylori* to the minimum inhibitory concentration of the cobalt salt against other bacteria normally present in the intestinal tract of mammals is greater than 10:1.

23. A method of selectively treating a gastrointestinal infection caused by *Helicobacter pylori* (*H. pylori*) in a mammal, which comprises the step of administering to a mammal a therapeutically effective amount of a pharmaceutical composition, wherein the composition comprises a cobalt salt and a proton pump inhibitor or an $H_2$ receptor antagonist together with a pharmaceutically acceptable diluent or carrier and wherein said cobalt salt comprises an anion of an acid having a pKa of less than about 4 and/or which is monovalent, wherein the cobalt salt is selective for *H. pylori* at a pH of 3 to 5 and wherein the cobalt salt delivers cobalt ions in an uncomplexed form and wherein a therapeutic amount of the cobalt salt selectively targets *H. pylori* infections.

24. The method of claim 23, wherein the cobalt salt is selective for *H. pylori* such that it is more toxic for *H. pylori* than other bacteria present in the gut, wherein the bacteria are selected from the group consisting of *Klebsiella*, coagulase negative *staphylococcus, Enterococcus faecalis, Enterococcus faecium*, and *Escherichia coli*.

25. The method of claim 24, wherein the bacteria are *Klebsiella*, coagulase negative *staphylococcus, Enterococcus faecalis*, and *Enterococcus faecium*.

26. The method of claim 23, wherein the ratio of minimum inhibitory concentration for the cobalt salt against *H. pylori* to the minimum inhibitory concentration of the cobalt salt against other bacteria normally present in the intestinal tract of mammals is greater than 10:1.

* * * * *